US006605113B2

(12) United States Patent
Wilk (10) Patent No.: US 6,605,113 B2
(45) Date of Patent: *Aug. 12, 2003

(54) VASCULAR GRAFT BYPASS (75) Inventor: Peter J. Wilk, New York, NY (US)

(73) Assignee: Percardia Inc., Nashua, NH (US)

( * ) Notice: Subject to any disclaimer, the term of this patent is extended or adjusted under 35 U.S.C. 154(b) by 6 days.

This patent is subject to a terminal disclaimer.

(21) Appl. No.: 09/828,793

(22) Filed: Apr. 10, 2001

(65) Prior Publication Data
US 2001/0037149 A1 Nov. 1, 2001

Related U.S. Application Data (63) Continuation of application No. 09/368,483, filed on Aug. 4, 1999, now Pat. No. 6,253,768.

(51) Int. Cl.[7] .............................. A61F 2/06; A61B 19/00
(52) U.S. Cl. .......................... 623/1.24; 128/898; 604/8
(58) Field of Search ................................ 128/898, 673, 128/897, 672, 748, 772, 774; 604/8; 606/192; 600/7, 15, 16; 623/1.24

(56) References Cited

U.S. PATENT DOCUMENTS

| 4,086,665 A | 5/1978 | Poirier |
| 4,503,568 A | 3/1985 | Madras |
| 4,546,499 A | 10/1985 | Possis et al. |
| 4,562,597 A | 1/1986 | Possis et al. |
| 4,733,665 A | 3/1988 | Palmaz |
| 4,769,029 A | 9/1988 | Patel |
| 5,135,467 A | 8/1992 | Citron |
| 5,193,546 A | 3/1993 | Shaknovich |
| 5,258,008 A | 11/1993 | Wilk |
| 5,287,861 A | 2/1994 | Wilk |
| 5,330,486 A | 7/1994 | Wilk |
| 5,409,019 A | 4/1995 | Wilk |

(List continued on next page.)

FOREIGN PATENT DOCUMENTS

| EP | 0 876 803 | 11/1998 |
| EP | 1 097 676 | 5/2001 |
| EP | 1 166 721 A2 | 1/2002 |
| GB | 2 316 322 | 2/1998 |
| WO | WO 96/25886 | 8/1996 |
| WO | 97/13463 | 4/1997 |
| WO | 97/13471 | 4/1997 |
| WO | 97/27893 | 8/1997 |
| WO | 97/27897 | 8/1997 |
| WO | 97/27898 | 8/1997 |
| WO | WO 97/31590 | 9/1997 |
| WO | 97/32551 | 9/1997 |

(List continued on next page.)

OTHER PUBLICATIONS

Gardner, M.D. et al., "An Experimental Anatomic Study of Indirect Myocardial Revascularization," *Journal of Surgical Research*, May 1971, vol. 11, No. 5, pp. 243–247.

Palmaz et al., "Expandable Intrahepatic Portacaval Shunt Stents: Early Experience in the Dog," *AJR*, 1985, vol. 145, pp. 821–825.

(List continued on next page.)

Primary Examiner—Paul B. Prebilic
(74) Attorney, Agent, or Firm—Finnegan, Henderson, Farabow, Garrett & Dunner, LLP (57) ABSTRACT Improved methods of treatment of diseased or occluded vascular grafts in patients having undergone coronary artery bypass or other bypass surgery are disclosed. Deployment of a conduit in the myocardium at a site distal to the site of attachment of the coronary artery bypass graft allows oxygenated blood to flow from a chamber in the heart directly into the coronary artery, bypassing blockages in the coronary artery and the graft originally used to bypass the coronary artery. To ensure proper positioning, the conduit is delivered through the graft to the myocardium. A new lining for the existing vein graft and methods of delivery are also disclosed.

17 Claims, 6 Drawing Sheets

U.S. PATENT DOCUMENTS

| | | |
|---|---|---|
| 5,429,144 A | 7/1995 | Wilk |
| 5,443,497 A | 8/1995 | Venbrux |
| 5,456,712 A | 10/1995 | Maginot |
| 5,456,714 A | 10/1995 | Owen |
| 5,470,320 A | 11/1995 | Tifenbrun et al. |
| 5,571,167 A | 11/1996 | Maginot |
| 5,655,548 A | 8/1997 | Nelson et al. |
| 5,662,124 A | 9/1997 | Wilk |
| 5,676,670 A | 10/1997 | Kim |
| 5,695,504 A | 12/1997 | Gifford, III et al. |
| 5,702,412 A | 12/1997 | Popov et al. |
| 5,746,709 A | 5/1998 | Rom et al. |
| 5,755,682 A | 5/1998 | Knudson et al. |
| 5,758,663 A | 6/1998 | Wilk et al. |
| 5,797,920 A | 8/1998 | Kim |
| 5,797,933 A | 8/1998 | Snow et al. |
| 5,797,946 A | 8/1998 | Chin |
| 5,800,522 A | 9/1998 | Campbell et al. |
| 5,810,836 A | 9/1998 | Hussein et al. |
| 5,817,113 A | 10/1998 | Gifford, III et al. |
| 5,824,071 A | 10/1998 | Nelson et al. |
| 5,830,222 A | 11/1998 | Makower |
| 5,865,723 A | 2/1999 | Love |
| 5,875,782 A | 3/1999 | Ferrari et al. |
| 5,876,419 A | 3/1999 | Carpenter et al. |
| 5,878,751 A | 3/1999 | Hussein et al. |
| 5,893,848 A | 4/1999 | Negus et al. |
| 5,904,697 A | 5/1999 | Gifford, III et al. |
| 5,908,028 A | 6/1999 | Wilk |
| 5,908,029 A | 6/1999 | Knudson et al. |
| 5,922,022 A | 7/1999 | Nash et al. |
| 5,931,842 A | 8/1999 | Goldsteen et al. |
| 5,935,119 A | 8/1999 | Guy et al. |
| 5,944,019 A | 8/1999 | Knudson et al. |
| 5,971,993 A | 10/1999 | Hussein et al. |
| 5,976,159 A | 11/1999 | Bolduc et al. |
| 5,976,178 A | 11/1999 | Goldsteen et al. |
| 5,976,192 A | 11/1999 | McIntyre et al. |
| 5,980,548 A | 11/1999 | Evans et al. |
| 5,984,955 A | 11/1999 | Wisselink |
| 5,984,956 A | 11/1999 | Tweden et al. |
| 5,989,276 A | 11/1999 | Houser et al. |
| 5,989,287 A | 11/1999 | Yang et al. |
| 5,993,468 A | 11/1999 | Rygaard |
| 6,007,544 A | 12/1999 | Kim |
| 6,007,576 A | 12/1999 | McClellan |
| 6,026,814 A | 2/2000 | LaFontaine et al. |
| 6,027,497 A | 2/2000 | Daniel et al. |
| 6,029,672 A | 2/2000 | Vanney et al. |
| 6,035,856 A | 3/2000 | LaFontaine et al. |
| 6,042,581 A | 3/2000 | Ryan et al. |
| 6,045,565 A | 4/2000 | Ellis et al. |
| 6,053,911 A | 4/2000 | Ryan et al. |
| 6,053,924 A | 4/2000 | Hussein |
| 6,053,942 A | 4/2000 | Eno et al. |
| 6,056,743 A | 5/2000 | Ellis et al. |
| 6,063,082 A | 5/2000 | DeVore et al. |
| 6,067,988 A | 5/2000 | Mueller |
| 6,068,638 A | 5/2000 | Makower |
| 6,071,292 A | 6/2000 | Makower et al. |
| 6,076,529 A | 6/2000 | Vanney et al. |
| 6,080,163 A | 6/2000 | Hussein et al. |
| 6,092,526 A | 7/2000 | LaFontaine et al. |
| 6,093,166 A | 7/2000 | Knudson et al. |
| 6,102,941 A | 8/2000 | Tweden et al. |
| 6,106,538 A | 8/2000 | Shiber |
| 6,113,630 A | 9/2000 | Vanney et al. |
| 6,113,823 A | 9/2000 | Eno |
| 6,123,682 A | 9/2000 | Knudson et al. |
| 6,126,649 A | 10/2000 | VanTassel et al. |
| 6,139,541 A | 10/2000 | Vanney et al. |
| 6,155,264 A | 12/2000 | Ressemann et al. |
| 6,159,225 A | 12/2000 | Makower |
| 6,165,188 A | 12/2000 | Saadat et al. |
| 6,182,668 B1 | 2/2001 | Tweden et al. |
| 6,186,972 B1 | 2/2001 | Nelson et al. |
| 6,190,353 B1 | 2/2001 | Makower et al. |
| 6,193,726 B1 | 2/2001 | Vanney |
| 6,196,230 B1 | 3/2001 | Hall et al. |
| 6,197,050 B1 | 3/2001 | Eno et al. |
| 6,200,310 B1 | 3/2001 | Ben-Haim et al. |
| 6,213,126 B1 | 4/2001 | LaFontaine et al. |
| 6,214,041 B1 | 4/2001 | Tweden et al. |
| 6,217,575 B1 | 4/2001 | DeVore et al. |
| 6,223,752 B1 | 5/2001 | Vanney et al. |
| 6,231,587 B1 | 5/2001 | Makower |
| 6,237,607 B1 | 5/2001 | Vanney et al. |
| 6,238,406 B1 | 5/2001 | Ellis et al. |
| 6,250,305 B1 | 6/2001 | Tweden |
| 6,253,768 B1 * | 7/2001 | Wilk ........................ 128/898 |
| 6,253,769 B1 | 7/2001 | LaFontaine et al. |
| 6,254,564 B1 | 7/2001 | Wilk et al. |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,287,317 B1 | 9/2001 | Makower et al. |
| 6,290,728 B1 | 9/2001 | Phelps et al. |
| 6,302,875 B1 | 10/2001 | Makower et al. |
| 6,302,892 B1 | 10/2001 | Wilk |
| 6,330,884 B1 | 12/2001 | Kim |
| 6,350,248 B1 | 2/2002 | Knudson et al. |
| 6,361,519 B1 | 3/2002 | Knudson et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,390,098 B1 | 5/2002 | LaFontaine et al. |
| 6,406,488 B1 | 6/2002 | Tweden et al. |
| 6,406,491 B1 | 6/2002 | Vanney |
| 6,409,697 B2 | 6/2002 | Eno et al. |
| 6,409,751 B1 | 6/2002 | Hall et al. |
| 6,432,127 B1 | 8/2002 | Kim et al. |
| 6,443,158 B1 | 9/2002 | LaFontaine et al. |
| 6,447,539 B1 | 9/2002 | Nelson et al. |
| 6,454,704 B1 | 9/2002 | Knudson et al. |
| 6,454,760 B2 | 9/2002 | Vanney |
| 6,458,323 B1 | 10/2002 | Boekstegers |
| 2001/0002948 A1 | 6/2001 | Vanney |
| 2001/0004699 A1 | 6/2001 | Gittings et al. |
| 2001/0016700 A1 | 8/2001 | Eno et al. |
| 2001/0025643 A1 | 10/2001 | Foley |
| 2001/0027287 A1 | 10/2001 | Shmulewitz et al. |
| 2001/0034547 A1 | 10/2001 | Hall et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0047165 A1 | 11/2001 | Makower et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0049486 A1 | 4/2002 | Knudson et al. |
| 2002/0052637 A1 | 5/2002 | Houser et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |

| | | |
|---|---|---|
| 2002/0077566 A1 | 6/2002 | Laroya et al. |
| 2002/0092535 A1 | 7/2002 | Wilk |
| 2002/0095111 A1 | 7/2002 | Tweden et al. |
| 2002/0100484 A1 | 8/2002 | Hall et al. |
| 2002/0111672 A1 | 8/2002 | Kim et al. |
| 2002/0123698 A1 | 9/2002 | Garibotto et al. |
| 2002/0144696 A1 | 10/2002 | Sharkawy et al. |
| 2002/0161424 A1 | 10/2002 | Rapacki et al. |
| 2002/0165479 A1 | 11/2002 | Wilk |
| 2002/0165606 A1 | 11/2002 | Wolf et al. |

FOREIGN PATENT DOCUMENTS

| | | |
|---|---|---|
| WO | 97/43961 | 11/1997 |
| WO | 98/02099 | 1/1998 |
| WO | WO 98/03118 | 1/1998 |
| WO | 98/08456 | 3/1998 |
| WO | 98/10714 | 3/1998 |
| WO | 98/16161 | 4/1998 |
| WO | 98/19607 | 5/1998 |
| WO | WO 98/38939 | 9/1998 |
| WO | 98/38941 | 9/1998 |
| WO | WO 98/38942 | 9/1998 |
| WO | 98/44869 | 10/1998 |
| WO | 98/46115 | 10/1998 |
| WO | 98/46119 | 10/1998 |
| WO | 98/49963 | 11/1998 |
| WO | 98/49964 | 11/1998 |
| WO | 98/53759 | 12/1998 |
| WO | 98/55027 | 12/1998 |
| WO | 98/57590 | 12/1998 |
| WO | 98/57591 | 12/1998 |
| WO | WO 98/57592 | 12/1998 |
| WO | 98/06356 | 2/1999 |
| WO | WO 99/08603 | 2/1999 |
| WO | 99/08624 | 2/1999 |
| WO | 99/49793 | 3/1999 |
| WO | 99/17683 | 4/1999 |
| WO | 99/21490 | 5/1999 |
| WO | 99/21510 | 5/1999 |
| WO | 99/22655 | 5/1999 |
| WO | 99/25273 | 5/1999 |
| WO | WO 99/35979 | 7/1999 |
| WO | 99/36000 | 7/1999 |
| WO | 99/36001 | 7/1999 |
| WO | WO 99/37218 | 7/1999 |
| WO | 99/38459 | 8/1999 |
| WO | 99/40868 | 8/1999 |
| WO | 99/47071 | 9/1999 |
| WO | WO 99/48427 | 9/1999 |
| WO | 99/48545 | 9/1999 |
| WO | 99/49790 | 10/1999 |
| WO | 99/49910 | 10/1999 |
| WO | 99/51162 | 10/1999 |
| WO | WO 99/52475 | 10/1999 |
| WO | 99/53863 | 10/1999 |
| WO | 99/60941 | 12/1999 |
| WO | 99/62430 | 12/1999 |
| WO | 00/09195 | 2/2000 |
| WO | 00/12029 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 00/15275 | 3/2000 |
| WO | 00/18302 | 4/2000 |
| WO | 00/21436 | 4/2000 |
| WO | 00/21461 | 4/2000 |
| WO | 00/21463 | 4/2000 |
| WO | 00/24449 | 5/2000 |
| WO | 00/33725 | 6/2000 |
| WO | 00/41632 | 7/2000 |
| WO | 00/41633 | 7/2000 |
| WO | 00/45711 | 8/2000 |
| WO | WO 00/45886 | 8/2000 |
| WO | 00/49954 | 8/2000 |
| WO | 00/49956 | 8/2000 |
| WO | 00/56387 | 9/2000 |
| WO | 00/57814 | 10/2000 |
| WO | 00/66007 | 11/2000 |
| WO | 00/66009 | 11/2000 |
| WO | 00/66035 | 11/2000 |
| WO | 00/71195 | 11/2000 |
| WO | WO 01/10340 A1 | 2/2001 |
| WO | WO 01/10341 A2 | 2/2001 |
| WO | WO 01/10347 A1 | 2/2001 |
| WO | WO 01/10348 A1 | 2/2001 |
| WO | WO 01/10349 A1 | 2/2001 |
| WO | 01/17440 | 3/2001 |
| WO | WO 01/49187 A1 | 7/2001 |

OTHER PUBLICATIONS

Palmaz et al., "Expandable Intrahepatic Portacaval Shunt Stents in Dogs with Chronic Portal Hypertension," *AJR*, 1986, vol. 147, pp. 1251–1254.

Richter, M.D. et al., "Transjugular Intrahepatic Portacaval Stent–Shunt: Preliminary Clinical Results," *Radiology*, 1990, vol. 174, No. 3, pp. 1027–1030.

Zemel, M.D. et al., "Percutaneous Transjugular Portosystemic Shunt," *JAMA*, 1991, vol. 266, No. 3, pp. 390–393.

Massimo, M.D. et al., "Myocardial Revascularization by a New Method of Carrying Blood Directly from the Left Ventricular Cavity into the Coronary Circulation," *Journal of Thoracic Surgeons*, Aug. 1997, vol. 34, No. 2, pp. 257–264.

Lary, M.D. et al., "Myocardial Revascularization Experiments Using the Epicardium," *Archives of Surgery*, Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery*, Jul. 1969, vol. 58, No. 1, pp. 25–32.

Kuzela, M.D. et al., "Experimental evaluation fo direct transventricular revascularization," *The Journal of Thoracic and Cardiovascular Surgery*, Jun. 1969, vol. 57, No. 6, pp. 770–773.

Lary et al., "A method for creating a coronary–myocardial arter," *Surgery*, vol. 59, No. 6, Jun. 1966, pp. 1061–1064.

Anabtawi, M.D. et al., "Experimental evaluation of myocardial tunnelization as a method of myocardial revascularization," *The Journal of Thoracic and Cardiovascular Surgery*, Nov. 1969, pp. 638–646.

Urschel, Jr., M.D., et al., "Direct and indirect myocardial revascularization: Follow–up and appraisal." *Surgery*, vol. 6, No. 6, Dec. 1970, pp. 1087–1100.

Young, Jr. M.D., et al., "Preoperative Assessment of Left Ventricular Function in Patients Selected for Direct Myocardial Revascularization," *The Annals of Thoracic Surgery*, vol. 11, No. 5, May 1971, pp. 695–402.

Tweden et al., "Ventriculocoronary Artery Bypass (VCAB), a Novel Approach to Myocardial Revascularization," #2000–4653, Feb. 2000.

* cited by examiner

VASCULAR GRAFT BYPASS

This is a continuation of U.S. application Ser. No. 09/368,483, filed Aug. 4, 1999, now U.S. Pat. No. 6,253,768, which is incorporated herein by reference.

BACKGROUND OF THE INVENTION

1. Field of the Invention

This invention relates to an improved treatment of diseased or occluded vascular grafts in patients having undergone coronary artery bypass surgery.

2. Description of the Related Art

Coronary artery disease is a major problem in the U.S. and throughout the world. Coronary arteries as well as other blood vessels frequently become clogged with plaque, which at the very least impairs the efficiency of the heart's pumping action, and can lead to heart attack and death. In some cases, these arteries can be unblocked through noninvasive techniques such as balloon angioplasty. In more difficult cases, a bypass of the blocked vessel is necessary.

In a bypass operation, one or more venous segments are inserted between the aorta and the coronary artery. The inserted venous segments or transplants act as a bypass of the blocked portion of the coronary artery and thus provide for a free or unobstructed flow of blood to the heart. More than 500,000 bypass procedures are performed in the U.S. every year.

Such coronary artery bypass surgery, however, is a very intrusive procedure that is expensive, time-consuming and traumatic to the patient. The operation requires an incision through the patient's sternum (sternotomy), and that the patient be placed on a bypass pump so that the heart can be operated on while not beating. A saphenous vein graft is harvested from the patient's leg, another highly invasive procedure, and a delicate surgical procedure is required to piece the bypass graft to the coronary artery (anastomosis). Hospital stays subsequent to the surgery and convalescence are prolonged.

Over time, the vein graft itself may become diseased, stenosed, or occluded, similar to the original bypassed vessel. Old, diffusely diseased saphenous vein grafts are considered contraindications for angioplasty and atherectomy, severely limiting the options for minimally invasive treatment. Some diseased or occluded saphenous vein grafts are associated with acute ischemic syndromes, however, necessitating some form of intervention.

Thus, there is a need for an improved treatment of diseased or occluded grafts in patients having had coronary bypass surgery.

SUMMARY OF THE INVENTION

The preferred embodiments of the present invention address the need in the previous technology by providing a bypass system that restores the flow of oxygenated blood through the body. In a preferred embodiment, there is provided a method for bypassing an existing coronary artery bypass graft in a patient. A hollow conduit is inserted in the patient's myocardium at a location distal to the site of attachment of the graft, such that the conduit allows oxygenated blood to flow from the patient's heart directly into the coronary artery. The conduit is preferably delivered to the myocardium through the coronary artery bypass graft, to ensure that the conduit is positioned in the myocardium at a site that is distal to both the blockage in the coronary artery, and the site of attachment of the graft to the coronary artery. Locating the proper site, for example, through the left ventricle of the heart is very difficult. Thus, delivery of the conduit through the graft simultaneously solves both the problem of therapy and the problem of locating the proper site for insertion of the conduit in bypass patients.

The methods disclosed herein are preferably performed percutaneously, but other minimally invasive methods, and open-chest methods, can also be used. Prior to insertion into the patient, the conduit is preferably mounted on the distal end of a delivery catheter. The catheter is then inserted into the patient's vasculature, into the aorta, and then into the bypass graft for delivery into the myocardium.

Another embodiment of the invention includes a method for improving the patency of a coronary artery or other arterial or venous bypass graft. A lining is inserted in the hollow interior of the graft and preferably permanently attached to the graft. The lining can be made of various biocompatible materials, but a section of vein from the patient is preferred. The lining can be mounted on an inflatable balloon catheter, such as those used in angioplasty. The distal end of the catheter is delivered to the interior of the graft, and the balloon is inflated to expand the lumen of the graft and the lining. If desired, a delivery catheter can be used to deliver the catheter bearing the lining to the site of the graft. This method improves the "proximal flow" through the existing graft.

The methods disclosed herein for bypassing an existing graft and for improving the patency of an existing bypass graft can be used in combination, or in the alternative.

DETAILED DESCRIPTION OF THE PREFERRED EMBODIMENT

As is well known, the coronary artery branches off the aorta and is positioned along the external surface of the heart wall. Oxygenated blood flows from the heart to the aorta, and on to the rest of the body, some of the blood flowing into the coronary artery. In some individuals, plaque builds up within the coronary artery, blocking the free flow of blood and causing complications ranging from mild angina to heart attack and death.

In order to restore the flow of oxygenated blood through the coronary artery, bypass surgery is performed. One or more venous segments are used to join the aorta and a site in the coronary artery distal to the blockage. The inserted vascular segments act to bypass the blocked portion of the coronary artery and thus provide for a free or unobstructed flow of oxygenated blood from the heart. To perform the bypass, an incision is made through the patient's sternum (sternotomy), and the patient is placed on a bypass pump so that the heart and surrounding vessels can be operated on while not beating. Typically, a saphenous vein graft is harvested from the patient's leg, and the bypass graft is anastomosed to the aorta and to the coronary artery. It should be understood, however, that other arterial or venous segments may be used to perform the bypass and that other blocked vessels may be bypassed. The term "vascular graft" as used herein refers to any such venous or arterial segment used in any bypass procedure.

Figure 1:
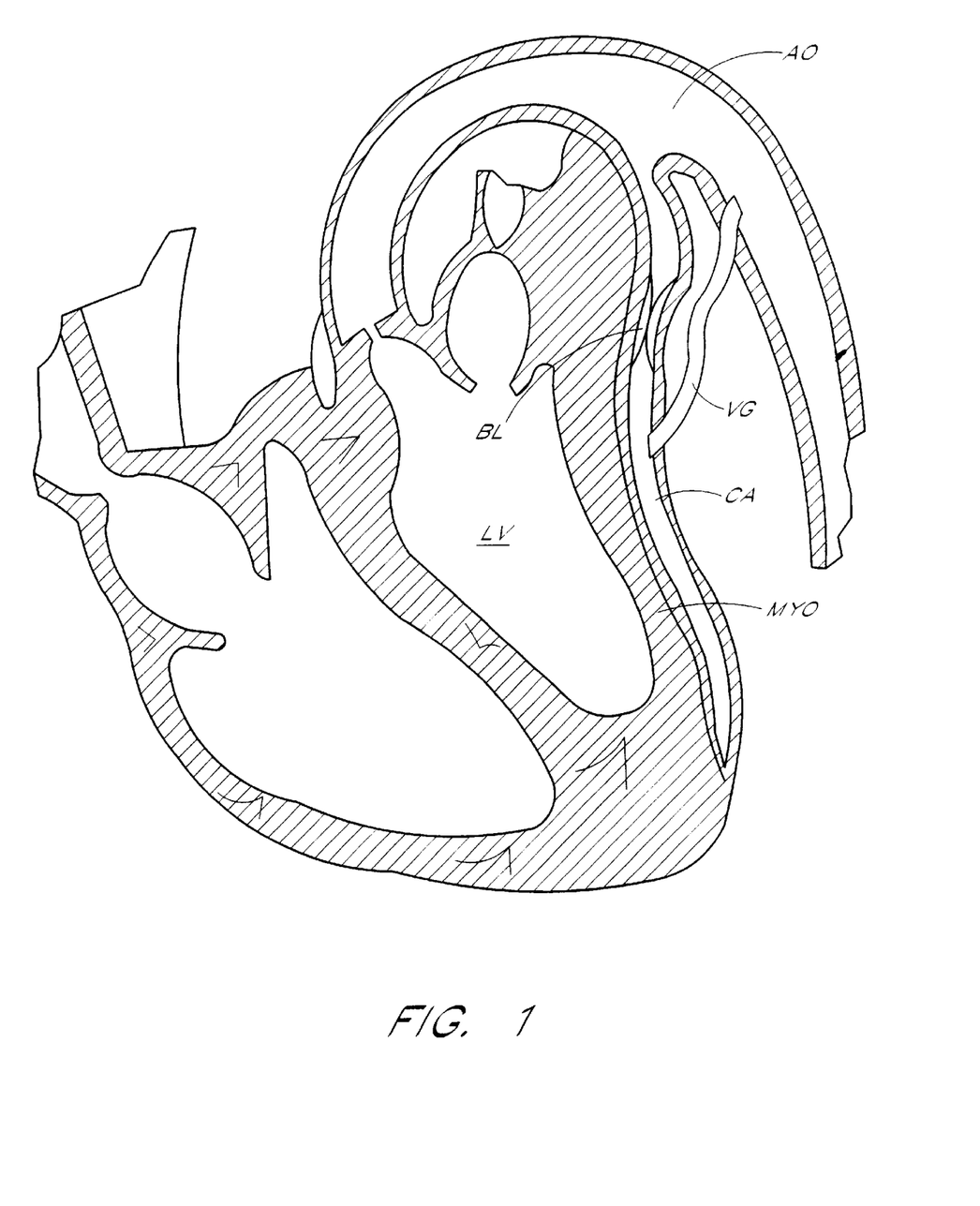
FIG. 1 is a cross-sectional view of a human heart, showing a saphenous vein graft used to bypass a blockage in the coronary artery.

FIG. 1 illustrates a human heart having a saphenous vein graft VG attached to the aorta AO and to the coronary artery CA at a site distal to the blockage BL in the coronary artery CA. As noted above, over time, the vein graft VG itself may become diseased, stenosed, or occluded, and intervention is necessary to once again restore the flow of oxygenated blood through the coronary artery CA.

Figure 2:
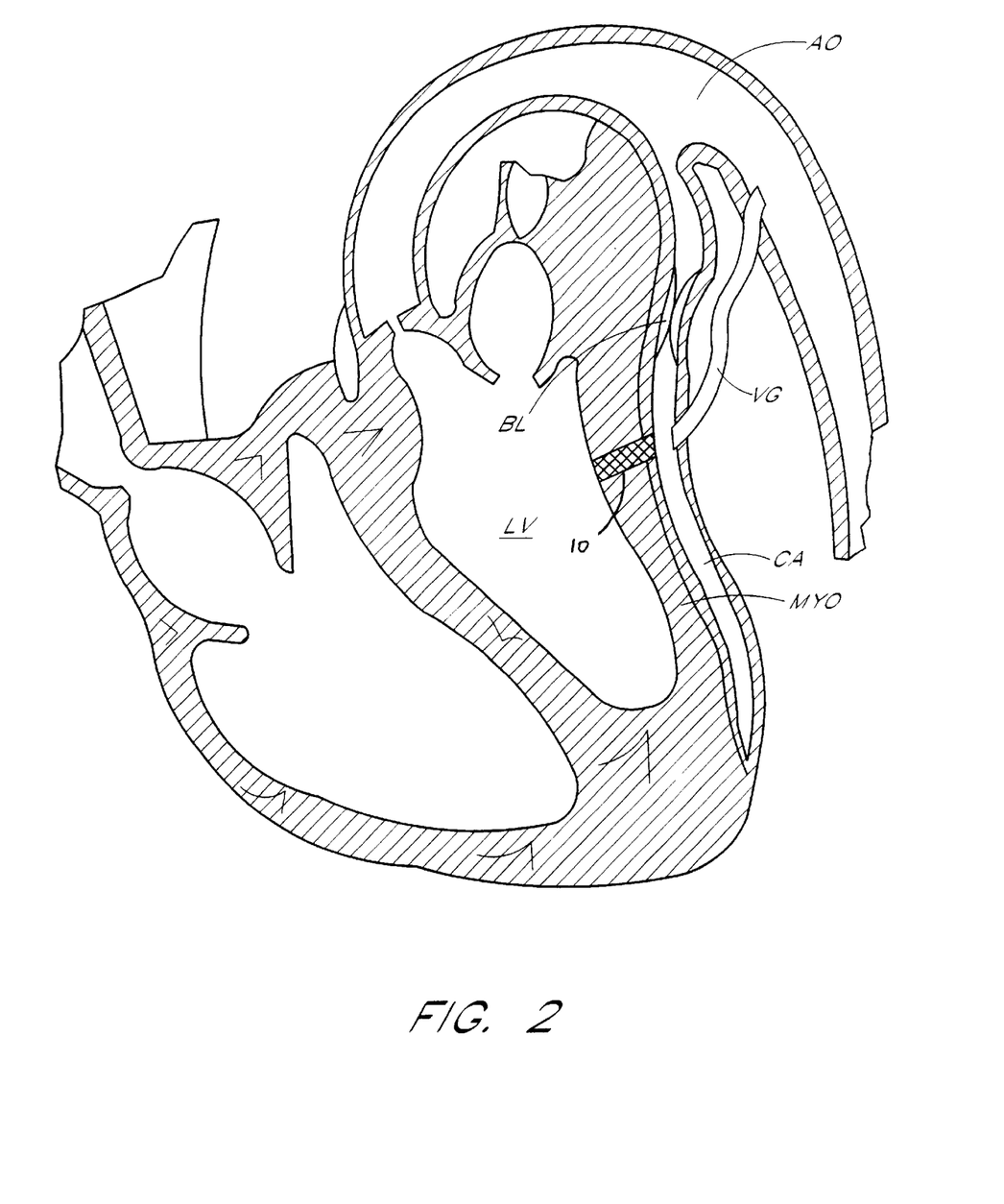
FIG. 2 is a cross-sectional view of a conduit placed in the myocardium to provide for the flow of oxygenated blood directly from the left ventricle in the heart into the coronary artery, bypassing the blockages in the coronary artery and the saphenous vein graft.

FIG. 2 illustrates means for bypassing the blockage BL in the coronary artery, as well as in the vein graft VG. A conduit 10 is positioned in the heart wall or myocardium MYO. Although the bypass described herein is from the left ventricle of the heart to the coronary artery, it should be understood that this is merely exemplary. The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. For example, in one preferred embodiment of the present invention, the conduit communicates from the left ventricle, through the myocardium, into the pericardial space, and then into the coronary artery. However, other preferred embodiments are disclosed, including direct transmyocardial communication from a left ventricle, through the myocardium and into the coronary artery. Thus, as emphasized above, the term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The present conduits can be deployed in a variety of methods consistent with sound medical practice including vascular or surgical deliveries, including minimally invasive techniques. For example, various preferred embodiments of delivery rods and associated methods may be used. In one embodiment, the delivery rod is solid and trocar-like. It may be rigid or semi-rigid and capable of penetrating the tissues of the patient and thereby form the conduit, in whole or in part, for purposes of fluid communication. In other preferred embodiments, the delivery rods may be hollow so as to form the conduits themselves (e.g., the conduits are preferably self-implanting or self-inserting) or have a conduit mounted thereon (e.g., the delivery rod is preferably withdrawn leaving the conduit installed). Thus, the preferred conduit device and method for installation is preferably determined by appropriate patient indications in accordance with sound medical practices.

The conduit 10, as illustrated in FIG. 2, preferably extends from the left ventricle LV of the heart to the coronary artery CA at a site that is distal to the site of the blockage BL. The conduit 10 is preferably made of a biocompatible material such as titanium, titanium alloys, nickel alloys, or biocompatible polymer. If desired, the conduit 10 can incorporate a valve that allows blood to flow freely from the left ventricle LV to the coronary artery CA but prevents the backflow of blood from the coronary artery 10 to the heart. Further details regarding conduits and conduit delivery systems are described in related patent applications: U.S. application Ser. No. 09/368,868, filed Aug. 4, 1999, entitled DELIVERY METHODS FOR LEFT VENTRICULAR CONDUIT, U.S. application Ser. No. 09/369,048, filed Aug. 4, 1999, entitled DESIGNS FOR LEFT VENTRICULAR CONDUIT, U.S. application Ser. No. 09/369,061, filed Aug. 4, 1999, entitled LEFT VENTRICULAR CONDUIT WITH BLOOD VESSEL GRAFT, U.S. application Ser. No. 09/368,393, filed Aug. 4, 1999, entitled VALVE DESIGNS FOR LEFT VENTRICULAR CONDUIT, U.S. application Ser. No. 09/369,039, filed Aug. 4, 1999, entitled LEFT VENTRICULAR CONDUITS TO CORONARY ARTERIES AND METHODS FOR CORONARY BYPASS, and U.S. application Ser. No. 09/368,644, filed Aug. 4, 1999, entitled BLOOD FLOW CONDUIT DELVIERY SYSTEM AND METHOD OF USE, and U.S. Pat. Nos. 5,429,144, and 5,662,124, the disclosures of which are all hereby incorporated by reference in their entirety.

In order to bypass the blockages in both the coronary artery CA and the vein graft VG, thereby providing for enhanced blood flow in the patient, the conduit 10 must be positioned at a site which is downstream or distal to the blockage BL in the coronary artery CA and the attachment site of the vein graft VG to the coronary artery CA. This allows oxygenated blood to flow directly from the left ventricle LV of the heart into the coronary artery CA and on to the rest of the body without encountering the blockage BL and without having to travel through the blocked vein graft VG. Although some proximal flow may occur through the vein graft, it is advantageous to place the conduit in a position which completely bypasses the blockage(s). The preferred positioning of the conduit 10 is illustrated in FIG. 2.

Figure 3A:
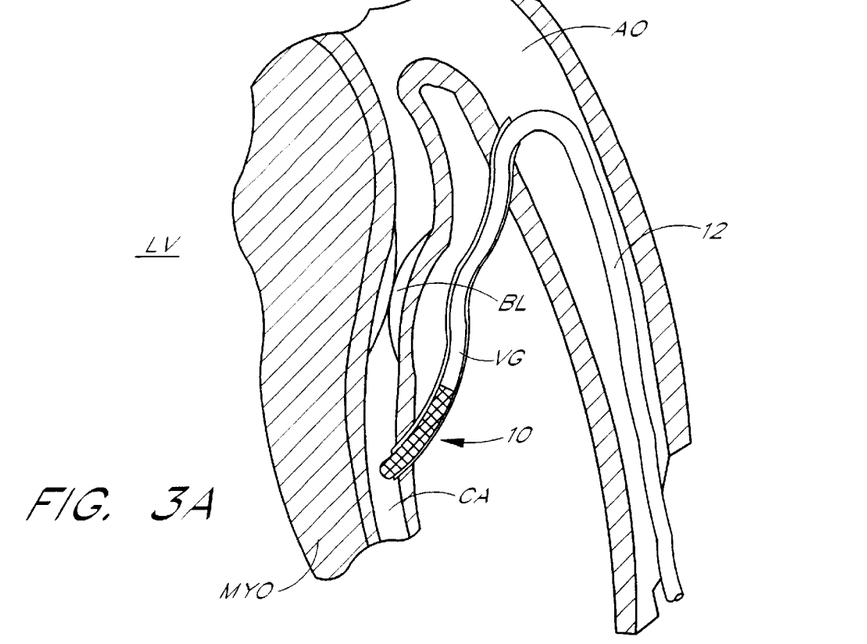
FIGS. 3A–C are enlarged views illustrating the delivery of the conduit through the saphenous vein graft and into the myocardium.
Figure 3B:
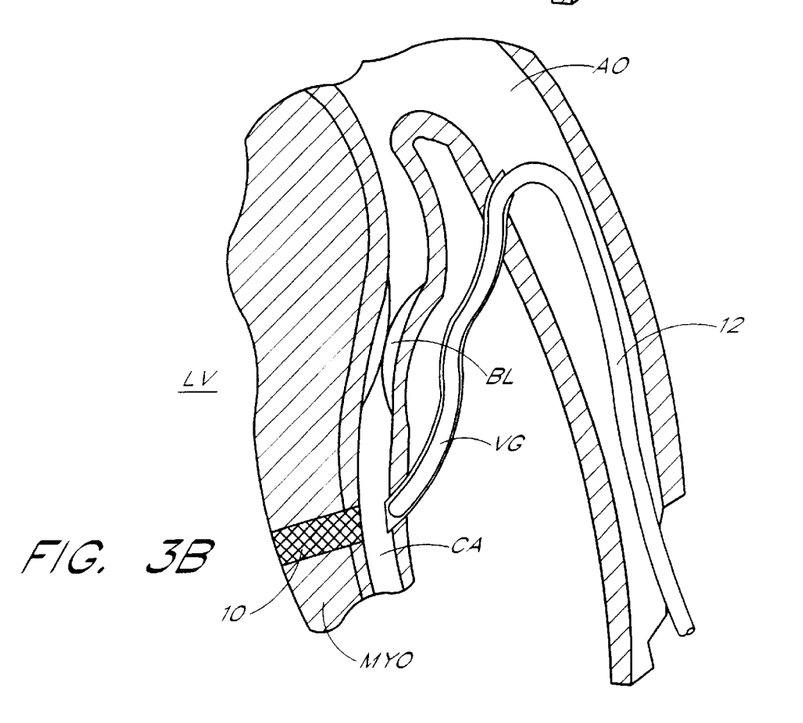
Figure 3C:
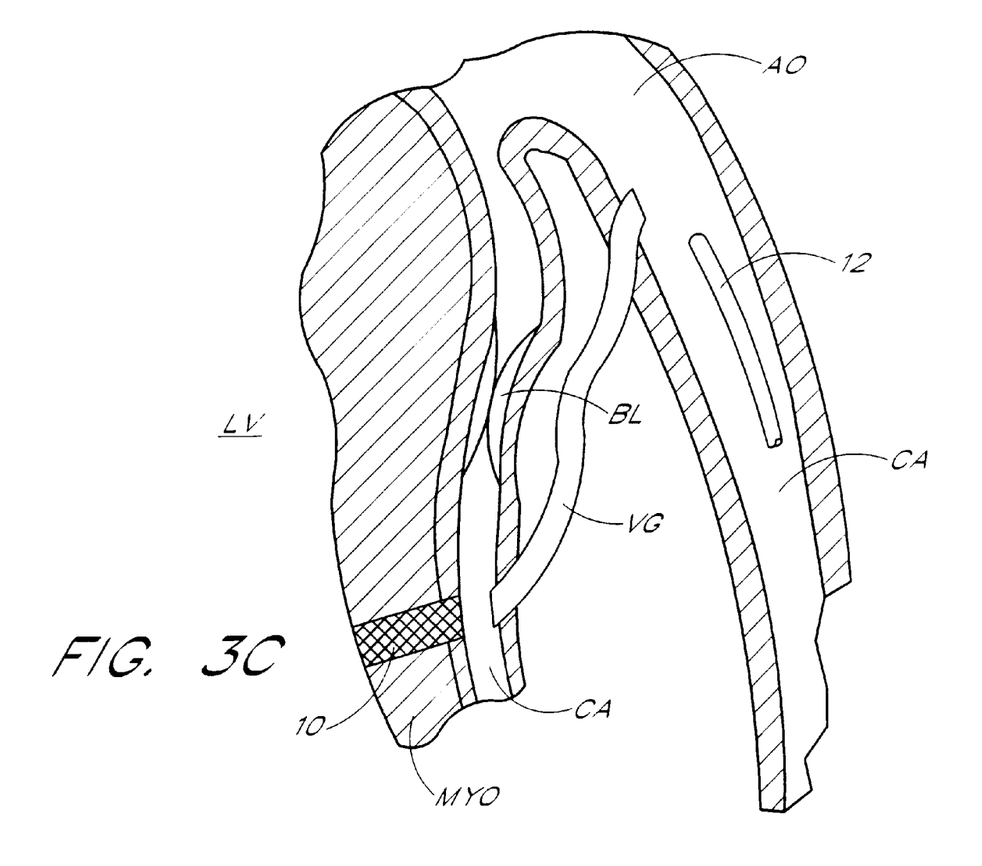

FIGS. 3A–3C depict a preferred method for delivery of the conduit 10 into the myocardium MYO. Although the figures illustrate the delivery of the conduit 10 percutaneously, it should be appreciated that the percutaneous approach is not essential to achieve many objects of the present invention, and therefore, an open-chest or other approach can also be used. In the preferred embodiment illustrated, the conduit 10 is delivered percutaneously, through the aorta AO and through the vein graft VG, thereby ensuring that both the original blockage BL in the coronary artery CA and the vein graft VG itself are bypassed. Other methods of delivery of the conduit 10 through the vein graft VG to a site in the myocardium MYO past both the blockage BL in the coronary artery CA and the site of attachment of the vein graft VG are also contemplated.

The conduit 10 is first mounted on the distal end of a steerable delivery catheter 12 (FIG. 3A). The catheter 12 is delivered into the patient's vasculature, such as through the femoral artery in the thigh, and through the aorta AO until it reaches the site of attachment of the vein graft VG. The catheter 12 is then delivered through the vein graft VG and into the coronary artery CA. The distal end of the catheter 12 is positioned adjacent the desired insertion point in the myocardium MYO. The conduit 10 is then inserted into the myocardium MYO, such that one end of the conduit 10 is positioned in the left ventricle LV of the heart, and the other end is positioned in the coronary artery CA (FIG. 3B). Methods of conduit delivery are described in detail in the above-referenced U.S. application Ser. No. 09/368,868, filed Aug. 4, 1999, entitled DELIVERY METHODS FOR LEFT VENTRICULAR CONDUIT, and in U.S. Pat. Nos. 5,429,144 and No. 5,409,019, all of which are hereby incorporated by reference in their entirety. The conduit 10 therefore provides for the shunting of oxygenated blood directly from the left ventricle LV of the heart into the coronary artery CA.

The conduit 10 can include anchoring means such as hooks, barbs, flanges or collars, or can be sutured, stapled or otherwise anchored in place to prevent conduit migration. The position of the conduit can be checked radiographically, and adjusted if necessary. As illustrated in FIG. 3C, after the conduit 10 has been properly positioned in the myocardium MYO, the delivery catheter 12 is withdrawn from the patient.

Another embodiment of the present invention is illustrated in FIGS. 4A–D. In this embodiment, an existing vascular graft is provided with a new, biocompatible lining, which allows for the free passage of blood therethrough. The lining can be formed of any biocompatible material, such as various polymers, but is preferably formed from a section of blood vessel, such as a vein, taken from the patient. The section of vein or other blood vessel harvested preferably contains one or more one-way valves, which occur naturally in the veins. In a preferred embodiment, the new vein section used to line the existing graft is obtained from the saphenous vein in the patient. Of course a blood vessel taken from a human or animal donor could also be used. For example, a fetal pig or piglet could be obtained and dissected to remove a section of the pulmonary artery having a pulmonic valve therein, or a section of the aorta having an aortic valve, or any other similar vessel having a naturally occurring valve system.

The vein section harvested is preferably sized so as to be approximately the same length as the original vein graft VG, but other lengths are also contemplated. The natural vein is biocompatible and therefore reduces the occurrence of problems associated with rejection and clotting. In addition, the vein section provides a natural valve system that is already in use throughout the body to prevent the backflow of blood. After the vein section has been harvested, it is mounted on the distal end of a catheter for insertion into the patient, as described below.

Figures 4A, 4B, 4C:
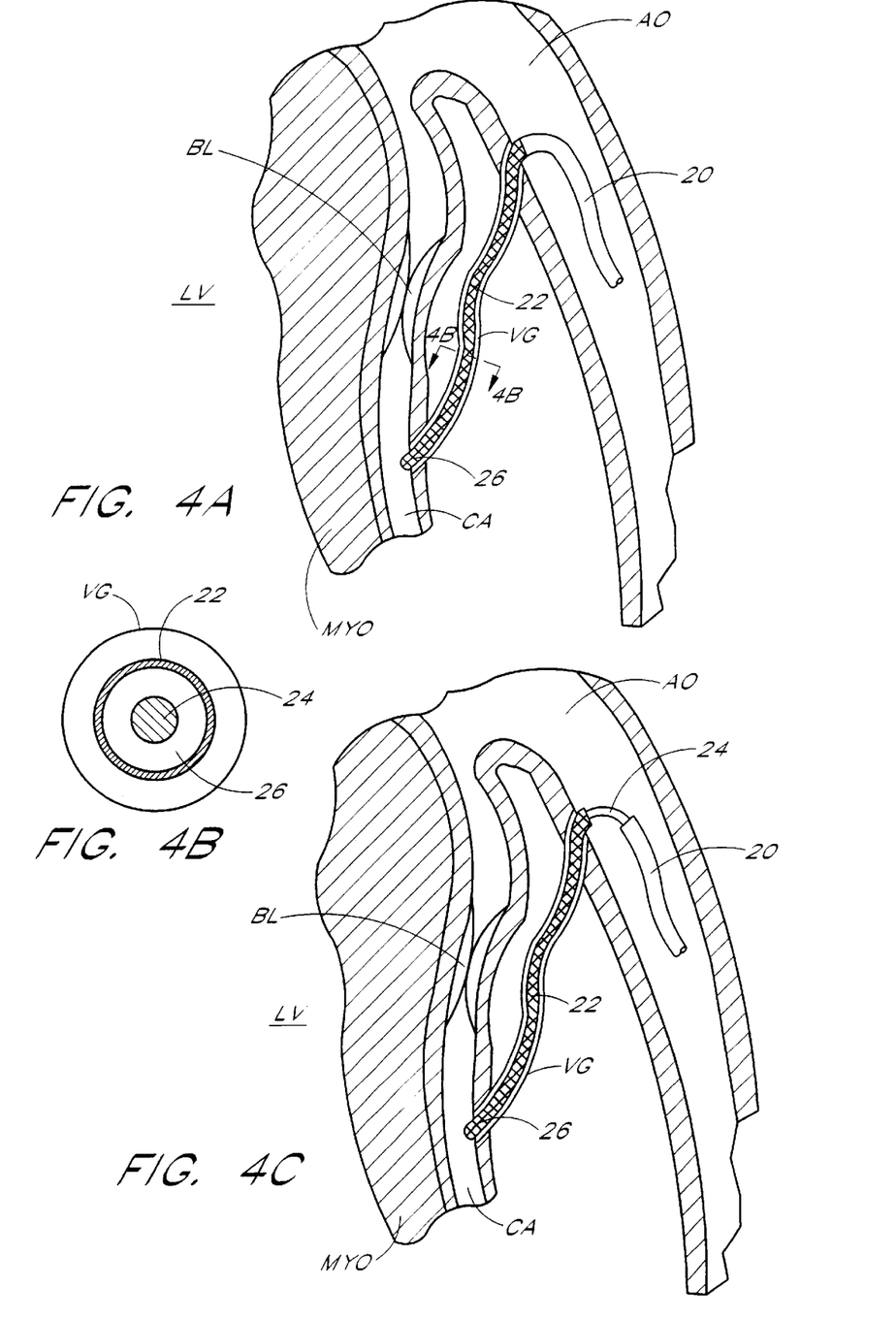
FIGS. 4A–E are enlarged views illustrating the delivery of a new vein lining into an existing vein graft used to bypass a blockage in the coronary artery.

Turning now to FIG. 4A, there is illustrated a steerable delivery catheter 20 having an inner lumen. A vein section 22 obtained as described above is mounted on the distal end of a second catheter 24, which is inserted through the lumen of the delivery catheter 20. The second catheter 24 preferably has an inflatable balloon 26 mounted on its distal end, over which the vein section 22 is concentrically mounted. Inflatable catheters are well known to these of skill in the art, and can be readily obtained from various commercial sources. The delivery catheter 20 and second catheter 24 are preferably delivered together into the patient's vasculature, such as through the femoral artery in the thigh, and through the aorta AO until they reach the site of attachment of the vein graft VG. The second catheter 24 bearing the vein section 22 is then delivered through the vein graft VG, as illustrated in FIG. 4B.

Figure 4D:
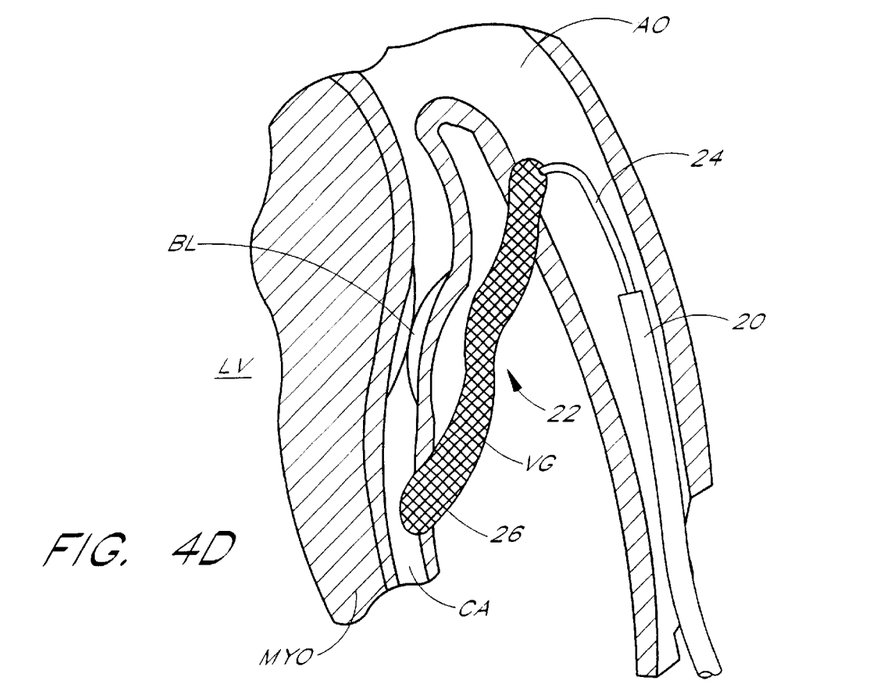
Figure 4E:
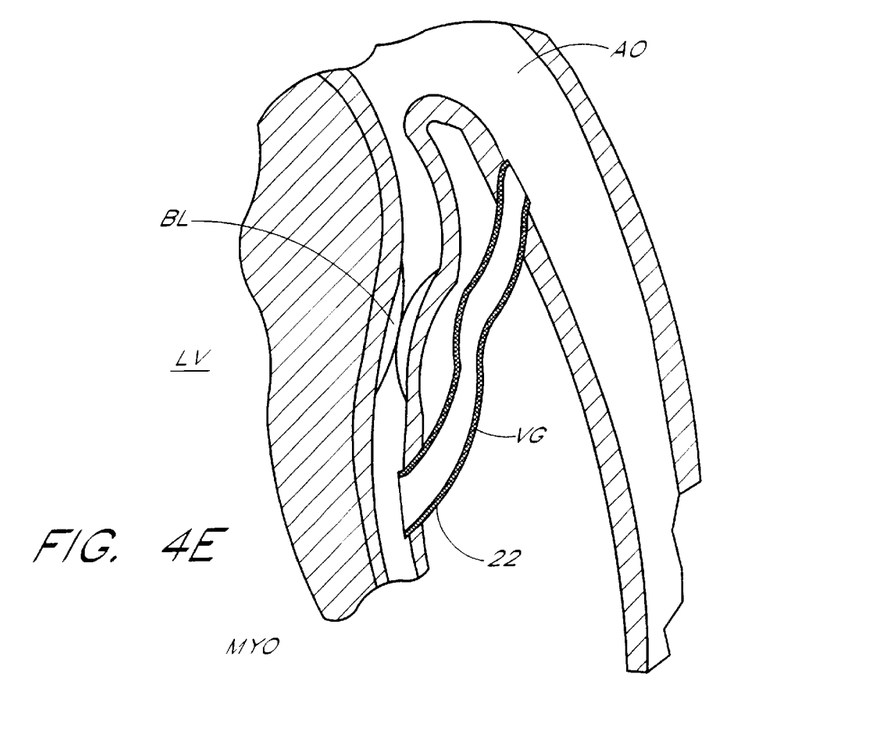

After the new vein section 22, mounted on the distal end of the second catheter 24, is delivered into the vein graft VG, the delivery catheter 20 is withdrawn, as illustrated in FIG. 4C. The second catheter 24 and new vein section 22 remain in position inside the vein graft VG. The balloon 26 at the distal end of the second catheter 24 is inflated as shown in FIG. 4D. Expansion of the balloon 26 forces the new vein section 22 against the interior of the existing vein graft VG, expanding the interior lumen in both the existing graft VG and the new vein section 22, opening a new passage for blood to flow through the vein graft VG. The balloon 26 is deflated, and the second catheter 24 is withdrawn from the patient, leaving the existing vein graft VG with a new vein lining, as illustrated in FIG. 4E.

Preferably, the new vein section 22 is attached to the existing vein graft VG or to the aorta AO at one end and to the coronary artery CA at the other end. The new vein section 22 can be attached by sutures, staples, or other attachment means.

The embodiments illustrated and described above are provided merely as examples of certain preferred embodiments of the present invention. Changes and modifications can be made to the embodiments presented herein by those skilled in the art without departure from the spirit and scope of the invention, as defined by the claims which follow.

What is claimed is:

1. A method for placing a conduit in a heart wall between a heart chamber and a coronary vessel, comprising:

providing a conduit on a distal end of a delivery catheter;

advancing the delivery catheter and the conduit through a bypass graft;

inserting the conduit in the heart wall between the heart chamber and the coronary vessel at a location proximate a site of attachment of the bypass graft; and anchoring the conduit in position within the heart wall.

2. The method of claim 1, wherein the coronary vessel is a coronary artery.

3. The method of claim 2, further comprising advancing the delivery catheter and the conduit from an aorta through the bypass graft and into the coronary artery.

4. The method of claim 3, further comprising advancing the conduit substantially transverse to the coronary artery.

5. The method of claim 1, wherein the bypass graft is a coronary artery bypass graft.

6. The method of claim 1, further comprising advancing the delivery catheter and the conduit percutaneously through the bypass graft.

7. The method of claim 1, wherein inserting the conduit comprises inserting the conduit in the heart wall such that blood flows directly from the heart chamber to the coronary vessel and bypasses the bypass graft.

8. The method of claim 1, wherein the conduit is chosen from a stent and a shunt.

9. The method of claim 1, wherein inserting the conduit includes inserting the conduit such that it opens at one end into the heart chamber and at an opposite end into the coronary vessel.

10. The method of claim 9, wherein inserting the conduit includes inserting the conduit between a left ventricle and a coronary artery.

11. The method of claim 1, further comprising removing the delivery catheter after the conduit has been placed in the heart wall.

12. The method of claim 1, further comprising providing the conduit with an anchoring mechanism chosen from hooks, barbs, flanges, and collars to anchor the conduit into position in the heart wall.

13. The method of claim 1, wherein anchoring the conduit includes suturing the conduit into position.

14. The method of claim 1, wherein the chamber is the left ventricle.

15. The method of claim 1, further comprising visualizing the position of the conduit in the heart wall during the insertion of the conduit.

16. The method of claim 15, wherein visualizing the position of the passage includes visualizing the position radiographically.

17. The method of claim 1, wherein anchoring the conduit includes stapling the conduit into position.

* * * * *